United States Patent [19]

Haak et al.

[11] Patent Number: 5,385,543
[45] Date of Patent: Jan. 31, 1995

[54] IONTOPHORETIC DELIVERY DEVICE AND METHOD OF HYDRATING SAME

[75] Inventors: Ronald P. Haak; J. Richard Gyory, both of San Jose; Felix Theeuwes, Los Altos; Robert M. Myers, Stanford, all of Calif.

[73] Assignee: Alza Corporation, Palo Alto, Calif.

[21] Appl. No.: 85,466

[22] Filed: Jun. 30, 1993

Related U.S. Application Data

[63] Continuation of Ser. No. 605,290, Oct. 29, 1990, abandoned.

[51] Int. Cl.$^6$ .............................................. A61N 1/30
[52] U.S. Cl. ...................................... 604/20; 607/151
[58] Field of Search ................ 604/20, 49; 607/149, 607/151

[56] References Cited

U.S. PATENT DOCUMENTS

| | | | |
|---|---|---|---|
| 3,982,529 | 9/1976 | Sato | 128/641 |
| 3,991,755 | 11/1976 | Vernon et al. | 128/172.1 |
| 4,141,359 | 2/1979 | Jacobsen et al. | 128/172.1 |
| 4,166,457 | 9/1979 | Jacobsen et al. | 604/20 |
| 4,250,878 | 2/1981 | Jacobsen et al. | 128/207.21 |
| 4,383,529 | 5/1983 | Webster | 604/20 |
| 4,398,545 | 8/1983 | Wilson | 128/798 |
| 4,419,092 | 12/1983 | Jacobsen et al. | 604/20 |
| 4,474,570 | 10/1984 | Ariura et al. | 604/20 |
| 4,731,049 | 3/1988 | Parsi | 604/20 |
| 4,764,164 | 8/1988 | Sasaki | 604/20 |
| 4,820,263 | 4/1989 | Spevak et al. | 604/20 |
| 4,842,577 | 6/1989 | Konno et al. | 604/20 |
| 4,940,456 | 7/1990 | Sibalis et al. | 604/20 |
| 5,087,241 | 2/1992 | Mathesen et al. | 604/20 |
| 5,087,242 | 2/1992 | Petelenz et al. | 604/20 |
| 5,156,591 | 10/1992 | Gross et al. | 604/20 |
| 5,158,537 | 10/1992 | Haak et al. | 604/20 |

FOREIGN PATENT DOCUMENTS

| | | | |
|---|---|---|---|
| 0411146 | 6/1991 | European Pat. Off. | A61N 1/30 |
| 2562800 | 4/1984 | France | A61M 37/00 |
| A2562800 | 10/1985 | France | A61M 37/00 |
| 3703321A1 | 3/1988 | Germany | A61N 1/30 |
| 3703321 | 3/1988 | Germany | A61N 1/30 |
| 410009 | 5/1934 | United Kingdom . | |
| WO/9009413 | 8/1990 | WIPO | A61N 1/30 |

OTHER PUBLICATIONS

Dorland's Pocket Medical Dictionary, 23rd Ed., p. 362; W. B. Saunders Company.
"Esperimentelle Studien über Elektroendosmose an uber lebender menschlicher Haut" by Von Hermann Rein, Jan. 7, 1924; Zeitschrift fur Biologie Bd. SI., J. F. Lebmanns Verlag, Munchen 1924.

*Primary Examiner*—C. Fred Rosenbaum
*Assistant Examiner*—Michael Rafa
*Attorney, Agent, or Firm*—D. Byron Miller; Steven F. Stone; Edward L. Mandell

[57] ABSTRACT

A dry-state iontophoretic drug delivery device (10, 20) is provided. The device has drug and electrolyte reservoirs (15, 16) which are initially in a non-hydrated condition. In one embodiment of the invention, a passageway (21, 22) is provided through the backing layer (13) and the electrode layer (11, 12) of both the donor electrode assembly (8) and the counter electrode assembly (9). Water or other liquid can be introduced through these passageways (21, 22) in order to hydrate the drug and electrolyte reservoirs (15, 16) and activate the device (10). In another embodiment of the device (20), the drug and electrolyte reservoirs (15, 16) are initially separated from their respective electrodes (11, 12). After the reservoirs (15, 16) are hydrated, they are placed in electrical contact with their respective electrodes (11, 12). By joining the reservoir (15, 16) to the electrode (11, 12) after hydration occurs, delamination problems are reduced.

45 Claims, 2 Drawing Sheets

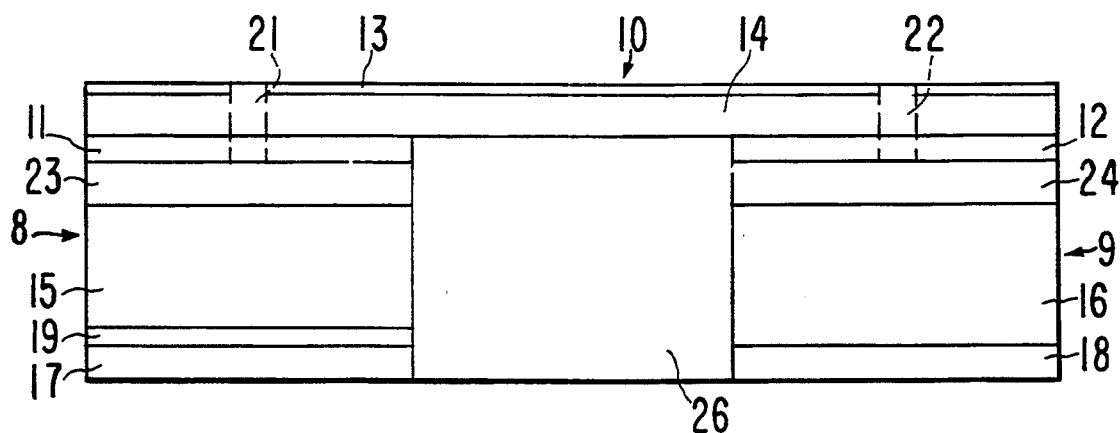
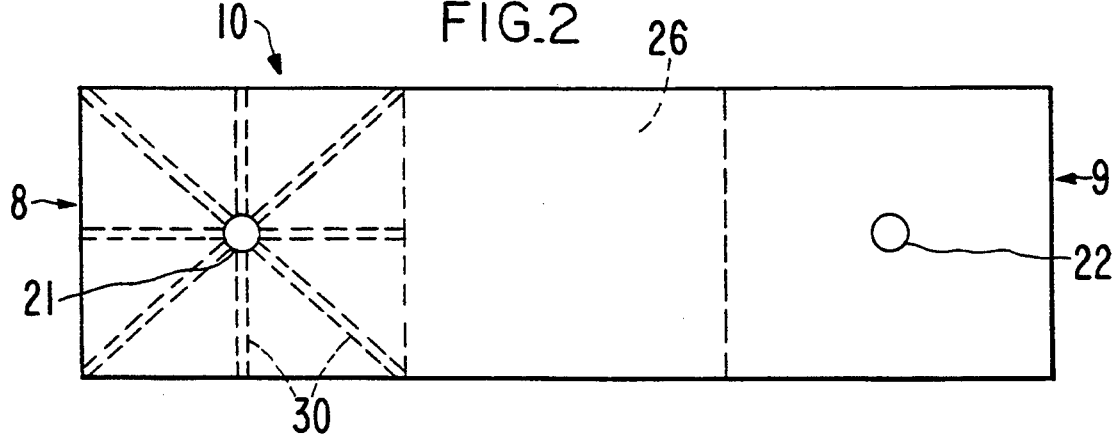
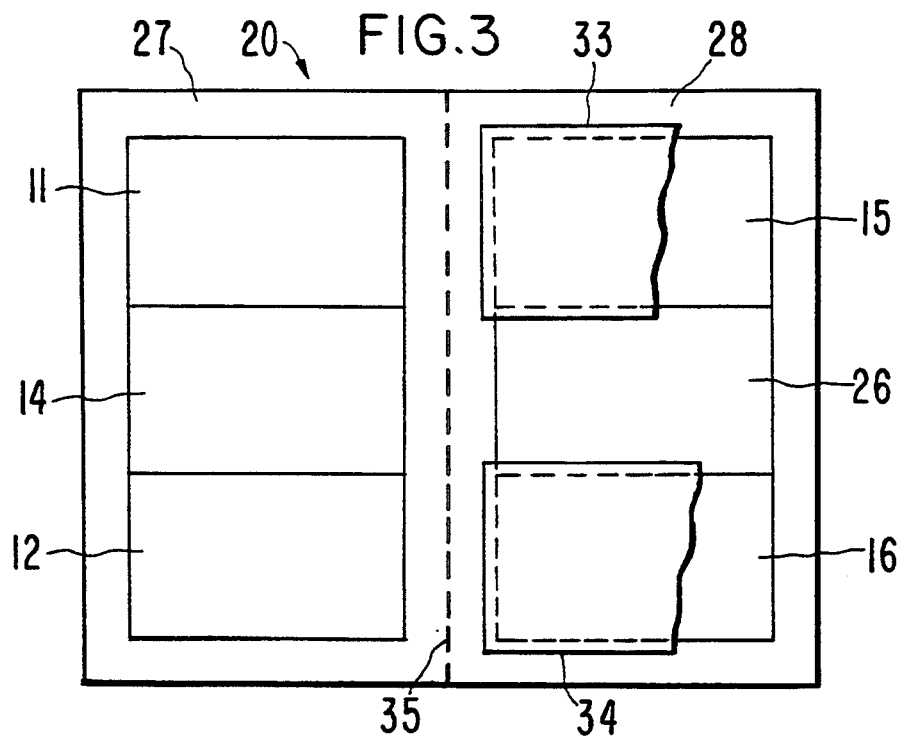

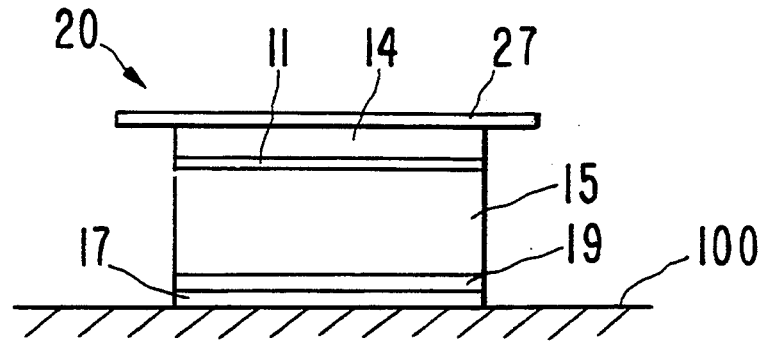
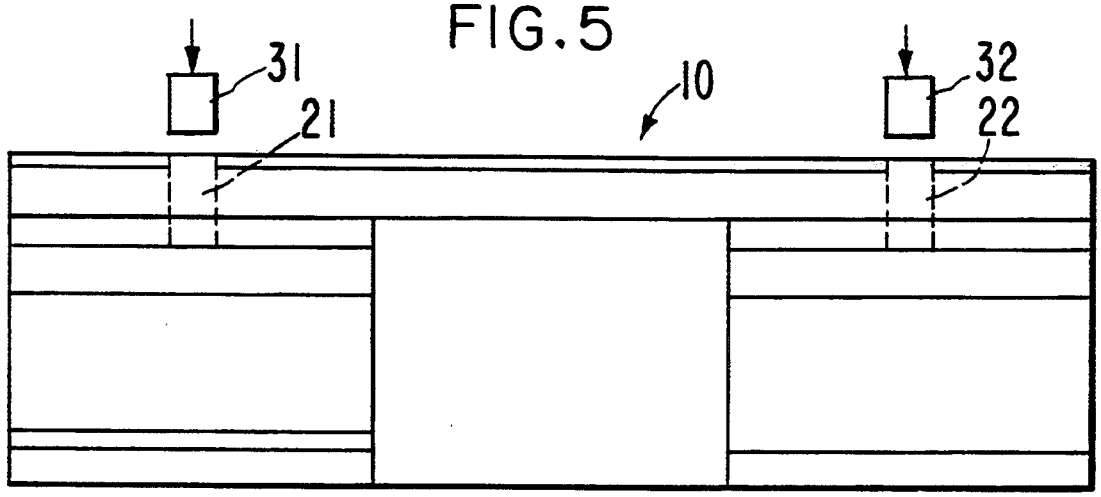

IONTOPHORETIC DELIVERY DEVICE AND METHOD OF HYDRATING SAME

This application is a continuation application Ser. No. 07/605,290, filed Oct. 29, 1990, and benefit of the filing date of said earlier filed application is claimed under 35 U.S.C. §120.

TECHNICAL FIELD

This invention relates to a device for delivering an agent transdermally or transmucosally by iontophoresis. More particularly, this invention relates to an electrically powered iontophoretic delivery device having electrodes which can be hydrated just before applying the device to the body.

BACKGROUND ART iontophoresis, according to Dorland's Illustrated Medical Dictionary, is defined to be "the introduction, by means of electric current, of ions of soluble salts into the tissues of the body for therapeutic purposes." Iontophoretic devices have been known since the early 1900's. British patent specification No. 410,009 (1934) describes an iontophoretic device which overcame one of the disadvantages of such early devices known to the art at that time, namely the requirement of a special low tension (low voltage) source of current which meant that the patient needed to be immobilized near such source. The device of that British specification was made by forming a galvanic cell from the electrodes and the material containing the medicament or drug to be delivered transdermally. The galvanic cell produced the current necessary for iontophoretically delivering the medicament. This ambulatory device thus permitted iontophoretic drug delivery with substantially less interference with the patient's daily activities.

More recently, a number of United States patents have issued in the iontophoresis field, indicating a renewed interest in this mode of drug delivery. For example, U.S. Pat. No. 3,991,755 issued to Vernon et al; U.S. Pat. No. 4,141,359 issued to Jacobsen et al; U.S. Pat. No. 4,398,545 issued to Wilson; and U.S. Pat. No. 4,250,878 issued to Jacobsen disclose examples of iontophoretic devices and some applications thereof. The iontophoresis process has been found to be useful in the transdermal administration of medicaments or drugs including lidocaine hydrochloride, hydrocortisone, fluoride, penicillin, dexamethasone sodium phosphate, insulin and many other drugs. Perhaps the most common use of iontophoresis is in diagnosing cystic fibrosis by delivering pilocarpine salts iontophoretically. The pilocarpine stimulates sweat production; the sweat is collected and analyzed for its chloride content to detect the presence of the disease.

In presently known iontophoretic devices, at least two electrodes are used. Both of these electrodes are disposed so as to be in intimate electrical contact with some portion of the skin of the body. One electrode, called the active or donor electrode, is the electrode from which the ionic substance, medicament, drug precursor or drug is delivered into the body by iontophoresis. The other electrode, called the counter or return electrode, serves to close the electrical circuit through the body. In conjunction with the patient's skin contacted by the electrodes, the circuit is completed by connection of the electrodes to a source of electrical energy, e.g., a battery. For example, if the ionic substance to be delivered into the body is positively charged (i.e., a cation), then the anode will be the active electrode and the cathode will serve to complete the circuit. If the ionic substance to be delivered is negatively charged (i.e., an anion), then the cathode will be the active electrode and the anode will be the counter electrode.

Alternatively, both the anode and cathode may be used to deliver drugs of opposite charge into the body. In such a case, both electrodes are considered to be active or donor electrodes. For example, the anode can deliver a positively charged ionic substance into the body while the cathode can deliver a negatively charged ionic substance into the body.

It is also known that iontophoretic delivery devices can be used to deliver an uncharged drug or agent into the body. This is accomplished by a process called electroosmosis. Transdermal delivery of nonionic drugs by the phenomenon of electroosmosis is described by Hermann Reiss in Zeitschrift fur Biologie, Bd. 81, pp 125–140 (1924) and the transdermal delivery of nonionic polypeptides by the phenomenon of electroosmosis is described in Sibalis et al. U.S. Pat. Nos. 4,878,892 and 4,940,456. Electroosmosis is the transdermal flux of a liquid solvent (e.g., the liquid solvent containing the uncharged drug or agent) which is induced by the presence of an electric field imposed across the skin by the donor electrode. As used herein, the terms "iontophoresis" and "iontophoretic" encompass both the delivery of charged ions as well as the delivery of uncharged molecules by the associated phenomenon of electroosmosis.

Iontophoretic delivery devices generally require a reservoir or source of the beneficial agent (which is preferably an ionized or ionizable agent or a precursor of such agent) to be iontophoretically delivered or introduced into the body. Examples of such reservoirs or sources of ionized or ionizable agents include a pouch or cavity as described in the previously mentioned Jacobsen U.S. Pat. No. 4,250,878, a porous sponge or pad as disclosed in Jacobsen et al. U.S. Pat. No. 4,141,359, or a preformed gel body as described in Webster U.S. Pat. No. 4,383,529 and Ariura et al. U.S. Pat. No. 4,474,570. Such drug reservoirs are electrically connected to the anode or the cathode of an iontophoresis device to provide a fixed or renewable source of one or more desired agents. Iontophoretic delivery devices which are attachable at a skin surface and rely on electrolyte fluids to establish electrical contact with such skin surfaces can be divided into at least two categories. The first category includes those devices which are prepackaged with the liquid electrolyte contained in the electrode receptacle. The second type of device uses dry-state electrodes whose receptacles are customarily filled with liquid drug/electrolyte immediately prior to application to the body. With both types of devices, the user currently experiences numerous problems which make their use both inconvenient and problematic.

With respect to the prefilled device, storage is a major concern. Many drugs have poor stability when in solution. Accordingly, the shelf life of prefilled iontophoretic drug delivery devices is unacceptably short. Corrosion of the electrodes and other electrical components is also a potential problem with prefilled devices. For example, the return electrode assembly will usually contain an electrolyte salt such as sodium chloride which over time can cause corrosion of metallic and other electrically conductive materials. Another problem with prefilled electrodes concerns maintaining the electrodes sterile and preventing microbial growth therein. This is a particular problem when the liquid used to conduct iontophoresis is water. Although antimicrobial agents can be added to the drug and/or electrolyte reservoirs of an iontophoretic delivery device, the addition of such agents tends to compromise the efficiency of agent delivery. Leakage is another serious problem with prefilled iontophoretic drug delivery devices. Leakage of drug or electrolyte from the electrode receptacle can result in an inoperative or defective state. Furthermore, such prefilled devices are difficult to apply because the protective seal which covers the electrode opening and retains the fluid within the receptacle cavity must be removed prior to application on the skin. After removal of this protective seal, spillage often occurs in attempting to place the electrode on the skin. Such spillage impairs the desired adhesive contact of the electrode to the skin and also voids a portion of the receptacle cavity. The consequent loss of drug or electrolyte fluid tends to disrupt electrical contact with the electrode plate contained therein and otherwise disrupts the preferred uniform potential gradient to be applied.

Although dry-state electrodes have numerous advantages in ease of storage, several problems remain. For example, the drug and electrolyte receptacles of such a device are conventionally filled through an opening prior to application of the device to the patient's skin. Therefore, the same problem of spillage and loss of drug or electrolyte upon application occurs as with the prefilled electrode.

Frequently, such electrodes are not well structured to develop the proper uniform current flow required in iontophoresis applications. Such nonuniform current flow may result from the occurrence of air pockets within the receptacle cavity at the skin surface. Such effects are particularly troublesome in iontophoresis applications, where a nonuniform current distribution may result in excessive skin irritation or "burning".

More recently, iontophoretic delivery devices have been developed in which the donor and counter electrode assemblies have a "multilaminate" construction. In these devices, the donor and counter electrode assemblies are each formed of multiple layers of (usually) polymeric matrices. For example, Parsi U.S. Pat. No. 4,731,049 discloses a donor electrode assembly having hydrophilic polymer based electrolyte reservoir and drug reservoir layers, a skin-contacting hydrogel layer, and optionally one or more semipermeable membrane layers. In addition, Ariura et al, U.S. Pat. No. 4,474,570 discloses a device wherein the electrode assemblies include a conductive resin film electrode layer, a hydrophilic gel reservoir layer, an aluminum foil conductor layer and an insulating backing layer.

The drug and electrolyte reservoir layers of iontophoretic delivery devices have typically been formed of hydrophilic polymers. See for example, Ariura et al, U.S. Pat. No. 4,474,570; Webster U.S. Pat. No. 4,383,529 and Sasaki U.S. Pat. No. 4,764,164. There are several reasons for using hydrophilic polymers. First, water is a biocompatible, highly polar solvent and therefore preferred for ionizing many drug salts. Secondly, hydrophilic polymer components (i.e., the drug reservoir in the donor electrode and the electrolyte reservoir in the counter electrode) can be hydrated while attached to the body by absorbing water from the skin or from a mucosal membrane. For example, skin contacting electrodes can be hydrated by absorbing sweat or water from transepidermal water loss. Similarly, electrodes attached to an oral mucosal membrane can be hydrated by absorbing saliva. Once the drug and electrolyte reservoirs become hydrated, ions are able to move through the reservoirs and across the tissue, enabling the device to deliver agent to the body. Hydrogels have been particularly favored for use as the drug reservoir matrix and electrolyte reservoir matrix in iontophoretic delivery devices, in part due to their high equilibrium water content and their ability to absorb water from the body. In addition, hydrogels tend to have good biocompatibility with the skin and with mucosal membranes. However, since many drugs and certain electrode components are unstable in the presence of water, iontophoretic drug delivery devices having a drug reservoir formed of a prehydrated hydrogel may also have an unacceptably short shelf life. One solution to the drug stability problem is to use hydrophilic polymer drug and electrolyte reservoirs which are in a substantially dry state, i.e. in a non-hydrated condition. The drug and/or electrolyte can be dry blended with the hydrophilic polymer and then cast or extruded to form a non-hydrated, though hydratable, drug or electrolyte containing reservoir. Unfortunately, the non-hydrated hydrophilic polymer components must first absorb sufficient quantities of water from the body before the device can operate to deliver drug. This delivery start-up period can take in excess of 8 hours. This delay makes many devices unsuited for their intended purpose. For example, when using an iontophoretic delivery device to apply a local anesthetic in preparation for a minor surgery (e.g., surgical removal of a mole), the surgeon and the patient must wait until the drug and electrolyte reservoirs of the delivery device become sufficiently hydrated before the anesthetic is delivered in sufficient quantities to induce anesthesia. Similar delays are encountered with other drugs.

In response to these difficulties, Konno et al. in U.S. Pat. No. 4,842,577 disclose in FIG. 4 an iontophoretic electrode assembly having a substantially non-hydrated drug containing matrix and a separate water reservoir which is initially sealed, using a foil sheet, from the drug containing portions of the electrode. Unfortunately, this electrode design is not only difficult to manufacture but also is subject to severe handling restrictions. In particular, there is a tendency for the foil seal to be inadvertently broken during manufacture, packaging and handling of the electrode. This can have particularly drastic consequences especially when the seal is broken during manufacture of the device. Once the seal is broken, water is wicked into the drug-containing reservoir which can cause degradation of the drug and/or other components before the device is ever used.

Another disadvantage of using non-hydrated hydrophilic polymer components is that they have a tendency to delaminate from other parts of the electrode assembly during hydration. For example, when utilizing a drug reservoir matrix or an electrolyte reservoir matrix composed of a hydrophilic polymer, the matrix begins to swell as it absorbs water from the skin. In the case of hydrogels, the swelling is quite pronounced. Typically, the drug or electrolyte reservoir is in either direct contact, or contact through a thin layer of an ionically conductive adhesive, with an electrode. Typically, the electrode is composed of metal (e.g., a metal foil or a thin layer of metal deposited on a backing layer) or a hydrophobic polymer containing a conductive filler (e.g., a hydrophobic polymer loaded with carbon fibers and/or metal particles). Unlike the hydrophilic drug and electrolyte reservoirs, the electrodes do not absorb water and do not swell. The different swelling properties of the hydrophilic reservoirs and the electrodes results in shearing along their contact surfaces. In severe cases, the shearing can result in the complete loss of electrical contact between the electrode and the drug/electrolyte reservoir resulting in an inoperable device.

DISCLOSURE OF THE INVENTION

Thus, it is an object of the present invention to provide an iontophoretic drug delivery device with electrodes which are manufactured in an initially non-hydrated or dry state but which can be quickly hydrated prior to placement on the body.

It is another object of this invention to provide an improved method of quickly hydrating the electrodes in an iontophoretic delivery device in order to minimize the "start-up" delay of an iontophoretic delivery device.

It is a further object of this invention to provide an iontophoretic drug delivery device which cannot be inadvertently hydrated prior to actual use.

It is a still further object of this invention to provide a method of hydrating the hydrophilic components of a dry state multilaminate iontophoresis electrode assembly without the delamination problems encountered with the prior art electrodes.

These and other objects are met by an electrically powered iontophoretic agent delivery device and a method of hydrating same. In accordance with one embodiment of the invention, the delivery device includes at least one multilaminate dry state electrode assembly and a source of electrical power which is electrically connected to the electrode assembly. The electrode assembly includes a reservoir layer comprised of a substantially non-hydrated hydratable matrix adapted to contain an agent to be delivered. The electrode assembly is adapted to be placed in agent transmitting relation with a body surface, such as intact skin or a mucosal membrane, for delivery of agent therethrough. The electrode assembly also includes an electrode layer in electrical contact with both the power source and the reservoir layer.

The electrode assembly has a preformed passageway through the electrode layer for admitting a hydrating liquid into the substantially non-hydrated matrix. The passageway establishes fluid communication between the exterior of the device and the non-hydrated matrix. The electrode assembly is activated by introducing a liquid from an external source through the preformed passageway and into the hydratable reservoir layer.

Preferably, the liquid comprises water. In the case of a donor electrode assembly, the agent preferably comprises a drug. In the counter electrode assembly, the agent preferably comprises an electrolyte salt. Most preferably, both the agent and the electrolyte salt are soluble in the liquid. The agent and/or the electrolyte salt may be present in the non-hydrated matrix either before hydration or maybe added to the non-hydrated matrix with the liquid at the time of hydration. When the non-hydrated matrix already contains the agent, the liquid preferably comprises deionized water. When the non-hydrated matrix initially contains no agent, the liquid preferably comprises an aqueous solution or suspension of a drug or an electrolyte salt. Most preferably, the matrix of the reservoir layer is comprised of a hydrophilic polymer.

In accordance with a second embodiment of the invention, a multilaminate dry state electrode assembly for an electrically powered iontophoretic agent delivery device, and a method of hydrating the electrode assembly, are provided. The electrode assembly is adapted to be placed in agent transmitting relation with a body surface such as intact skin or a mucosal membrane, for delivery of agent therethrough. The electrode assembly includes an electrode layer in electrical contact with an electrical power source and adapted to be placed in electrical contact with a reservoir layer. The reservoir layer is adapted to contain an agent to be delivered. The reservoir layer comprises a substantially non-hydrated, hydratable matrix which is initially separated from the electrode layer and the power source. The reservoir layer has an exposable surface for introducing a liquid thereto in order to hydrate the reservoir layer. After hydration, the reservoir layer is placed in electrical contact with the electrode layer.

Also provided is a method for hydrating the device. The method includes separating the reservoir layer from the electrode layer while the reservoir layer is in a substantially non-hydrated condition. A hydrating liquid is introduced into the reservoir layer in an amount sufficient to permit ion transport through the reservoir layer. Thereafter, the hydrated reservoir layer is secured in electrical contact with the electrode layer.

Preferably, the hydrating liquid comprises water. In the case of a donor electrode assembly, the agent preferably comprises a drug. In the counter electrode assembly, the agent preferably comprises an electrolyte salt. Most preferably, both the agent and the electrolyte salt are soluble in the liquid. The agent and/or the electrolyte salt may be present in the non-hydrated matrix either before hydration or may be added to the non-hydrated matrix with the liquid at the time of hydration. When the non-hydrated matrix already contains the agent, the liquid preferably comprises deionized water. When the non-hydrated matrix initially contains no agent, the liquid preferably comprises an aqueous solution or suspension of a drug or an electrolyte salt. Most preferably, the matrix of the reservoir layer is a hydrophilic polymer. This embodiment of the invention has particular utility where the hydrophilic polymer has a tendency to swell upon hydration. Most preferably, the hydrated reservoir layer is secured in electrical contact with the electrode layer after the swelling of the reservoir layer is substantially complete.

BRIEF DESCRIPTION OF THE DRAWINGS

FIG. 1 is a schematic side view of an iontophoretic drug delivery device according to the present invention;

FIG. 2 is a schematic top view of the device shown in FIG. 1;

FIG. 3 is a schematic top view of another embodiment of an iontophoretic delivery device according to the present invention;

FIG. 4 is a schematic end view of the device shown in FIG. 3, after assembly; and FIG. 5 is a schematic side view of another embodiment of an iontophoretic delivery device according to the present invention.

In the figures, like elements are designated by the same reference number in the several drawings.

MODES FOR CARRYING OUT THE INVENTION

FIG. 1 is a schematic view of an iontophoretic delivery device 10 for delivering a beneficial agent through a body surface such as intact skin or a mucosal membrane. Iontophoretic delivery device 10 includes a donor electrode assembly 8 and a counter electrode assembly 9. The donor electrode assembly 8 and the counter electrode assembly 9 are physically attached to insulator 26 and form a single self-contained unit. Insulator 26 prevents the electrode assemblies 8 and 9 from short circuiting the body by preventing electrical and/or ion transport between the electrode assemblies 8 and 9. Electrode assemblies 8 and 9 are connected in series, by appropriate electrical conductors, with an electrical power source. The power source and the electrical conductors are schematically shown as layer 14. The power source used to power device 10 is typically one or more low voltage batteries. A water impermeable backing layer 13 preferably covers layer 14 with its associated electrical components.

The donor electrode assembly 8 includes an electrode layer 11 and a reservoir layer 15. The reservoir 15 contains the beneficial agent to be iontophoretically delivered by device 10. A rate controlling membrane layer 19 is optionally positioned between the reservoir layer 15 and the body surface for controlling the rate at which the agent is delivered to the body surface or for preventing the delivery of agent to the body surface when the device is turned off. Counter electrode assembly 9 contacts the body surface at a location spaced apart from electrode assembly 8. Counter electrode assembly 9 includes an electrode layer 12 and a reservoir layer 16. Device 10 can be adhered to the body surface by means of ion-conducting adhesive layers 17 and 18. As an alternative to the ion-conducting adhesive layers 17 and 18 shown in FIG. 1, device 10 may be adhered to the body surface using an adhesive overlay. Any of the conventional adhesive overlays used to secure passive transdermal delivery devices to the skin may be used.

When the device 10 is in storage, no current flows because the device does not form a closed circuit. When the device 10 is placed on the skin or mucosal membrane of a patient and the electrode assemblies 8 and 9 are sufficiently hydrated to allow ions to flow through the various layers of electrode assemblies 8 and 9, the circuit between the electrodes is closed and the power source begins to deliver current through the device and through the body of the patient. The donor and counter electrode assemblies 8 and 9 normally include a strippable release liner, not shown, which is removed prior to application of electrode assemblies 8 and 9 to a body surface.

As shown in FIGS. 1 and 2, the donor electrode assembly 8 includes a preformed passageway 21 extending through the impermeable backing layer 13, the electronic component layer 14 and the donor electrode layer 11. The donor electrode assembly 8 optionally includes a layer 23 of a liquid-wicking material. Any liquid introduced through passageway 21 is quickly absorbed by layer 23 and wicked across the entire top surface of agent reservoir 15. Preferably, the passageway 21 is also filled with a similar liquid-wicking material. The passageway 21, optionally with the wicking layer 23, enables a liquid to be introduced through passageway 21 from the exterior of device 10 directly into the matrix of reservoir layer 15 in order to hydrate the matrix and optionally to hydrate the layers 23, 19 and/or 17 if they are present, and to activate the donor electrode assembly 8. In most cases the liquid used to hydrate the matrix of reservoir 15 will be water, but other liquids including non-aqueous liquids, can also be used to "hydrate" (i.e., activate) the matrix of reservoir layer 15. In the typical case where the liquid is water, the matrix of reservoir layer 15 will be at least partly composed of a hydrophilic material such as a hydrophilic polymer, a cellulosic sponge or pad, or other water retaining material. Most preferably, the matrix of reservoir layer 15 will be at least partly composed of a hydrophilic polymer of the type described hereinafter.

As an alternative to the wicking layer 23, the top surface of reservoir 15 may be provided with a plurality of grooves 30 in fluid communication with passageway 21. Grooves 30 distribute any liquid introduced through passageway 21 across the upper surface of reservoir 15. Grooves 30 are shown schematically in FIG. 2.

Similarly, a preformed passageway 22 extends through the electrode layer 12, the electronic component layer 14 and the impermeable backing layer 13. An optional liquid wicking layer 24 may be provided between reservoir 16 and electrode 12 in counter electrode assembly 9. Wicking layer 24 has a similar function to wicking layer 23 in the donor electrode assembly 8. Passageway 22 and wicking layer 24 establish fluid communication between the exterior of device 10 and the non-hydrated matrix of reservoir layer 16. The passageway 22, optionally with the wicking layer 24, enables a liquid to be introduced through passageway 22 from the exterior of device 10 directly into the matrix of reservoir layer 16 in order to hydrate the matrix, and optionally to hydrate the layers 24 and/or 18 if there are present, and to activate the counter electrode assembly 9. As with the donor electrode assembly 8, the liquid used to hydrate the matrix of reservoir layer 16 will typically be water, although other liquids including non-aqueous liquids, can also be used. As an alternative to layer 24, the top surface of electrolyte reservoir layer 16 may be provided with a plurality of grooves similar to grooves 30 shown in reservoir layer 15.

Preferably, as shown in FIG. 5, removable plugs 31 and 32 are provided to seal the openings to passageways 21 and 22, respectively. Plugs 31 and 32 may be formed of a material such as wax, rubber, polymer resin or a similar material which is effective to form a seal with passageways 21 and 22. Most preferably, plugs 31 and 32 form a water-tight seal with passageways 21 and 22, respectively. Plugs 31 and 32 help prevent evaporative liquid loss from the hydrated layers 15, 16, 17, 18, 19, 23 and 24 and thereby prevents these layers from drying out. Plugs 31 and 32 also enable device 10 to be worn on the body without danger of admitting liquids, such as ordinary tap water from bathing, containing extraneous ions or other contaminants into the reservoir layers 15 and 16.

In accordance with the present invention, at least one of electrode assemblies 8 and 9, and preferably both electrode assemblies 8 and 9 are initially in a substantially dry state. Thus, the various ion transporting layers making up electrode assemblies 8 and 9 are initially in a non-hydrated condition. As used herein, the terms "dry state" and "non-hydrated" mean that the particular layer contains an insufficient amount of liquid to permit ion transport therethrough. For example, the ion transmitting layers of donor electrode assembly 8 include reservoir layer 15 and optional layers 17, 19 and 23. In order for donor electrode assembly 8 to be considered a "dry state" electrode, none of layers 15, 17, 19 and 23 are sufficiently hydrated to allow ion transport therethrough.

Similarly, in order for counter electrode assembly 9 to be considered a "dry state" electrode, neither reservoir layer 16 nor optional layers 18 and 24 contains sufficient liquid to allow ion transport therethrough.

In order to be considered "non-hydrated," reservoir layers 15 and 16 should generally contain less than about 10 wt % liquid, preferably less than about 5 wt % liquid and most preferably less than about 1 wt % liquid.

In order to activate delivery device 10, reservoir layers 15 and 16, as well as the optional adhesive layers 17 and 18 and membrane layer 19, must become sufficiently hydrated to enable agent to be transported therethrough by iontophoresis. In order to hydrate reservoir layers 15 and 16, as well as the optional adhesive layers 17 and 18 and membrane layer 19, a liquid (typically water) is introduced through passageways 21 and 22. As shown in FIGS. 1 and 2, passageways 21 and 22 pass completely through the outer backing layer 13, the electronic component layer 14 and the electrode layers 11 and 12, respectively. Thus, the liquid can be introduced into passageways 21 and 22 simply by pouring the liquid directly into the openings of passageways 21 and 22 in the top of the device 10.

In most cases, the liquid introduced into device 10 through passageways 21 and 22 will be composed at least in part of water. However, it is well within the scope of the present invention to "hydrate" the reservoir layers 15 and 16 using other liquids including non-aqueous liquids such as alcohols and glycols. Accordingly, as used herein, the term "hydrate" refers to the addition of either aqueous or non-aqueous based liquids through passageways 21 and 22. Furthermore, in those instances where the non-hydrated reservoir layers 15 and/or 16 initially contain no drug or electrolyte, the hydrating liquid may comprise a liquid solution or suspension of the drug or electrolyte.

Turning now to FIGS. 3 and 4, there is shown an alternate embodiment of an iontophoretic agent delivery device, designated by the numeral 20, according to the present invention. FIG. 3 shows the structure of device 20 while in its initial non-hydrated condition. Reservoir layers 15 and 16 are separated from their respective electrode layers 11 and 12 and the electronic component layer 14. Thus, initially device 20 is separated into two parts. The left hand part includes the electronic component layer 14 and the electrode layers 11 and 12, all of which are laminated onto a sheet 27 of a preferably water impermeable backing material. The right side of device 20 includes reservoir layers 15 and 16 separated by insulator 26 and optionally ion-conducting adhesive layers 17 and 18, membrane layer 19 and wicking layers 23 and 24, all of which are laminated onto sheet 28, also of a preferably water impermeable backing material. A weakened score line 35 divides sheet 27 from sheet 28. As shown in FIG. 3, release liners 33 and 34 are provided to cover the reservoir layers 15 and 16, respectively.

Device 20 is manufactured with reservoir layers 15 and 16, along with any optional wicking layers, membrane layers and/or ion conducting adhesive layers, in a substantially non-hydrated condition. When device 20 is ready to be used, the release liners 33 and 34 are removed, thereby exposing reservoir layers 15 and 16. A hydrating liquid is then poured directly onto reservoir layers 15 and 16. Optionally, a wicking material, or liquid carrying grooves (not shown in FIG. 3) can be provided on the top surface of either or both of reservoir layers 15 and 16.

In this embodiment, reservoir layers 15 and 16 are preferably comprised of a material which becomes tacky once hydrated, e.g., a tacky hydrogel. Alternatively, the top surface of reservoir layers 15 and 16 can also be coated with a water-conducting and ion-conducting adhesive layer.

Once reservoir layers 15 and 16 become sufficiently hydrated to allow agent transport therethrough, sheet 28 is separated from sheet 27 by tearing along score line 35. The right side of the device is then placed directly over the left side of the device such that the reservoir layer 15 is in electrical contact with electrode layer 11 and the reservoir layer 16 is in electrical contact with electrode layer 12. Electrical contact between reservoir layers 15 and 16 and electrode layers 11 and 12, respectively, is maintained due to the tacky nature of layers 15 and 16, or alternatively by an adhesive applied on the top surfaces of layers 15 and 16. Thereafter, sheet 28 is removed and the device 20 is placed on a body surface 100 as shown in FIG. 4. FIG. 4 is an end view of device 20 and accordingly shows only the layered configuration of the "donor" electrode assembly. It will be understood that device 20, in its assembled condition, likewise contains an insulator 26 and a counter electrode assembly 9 similar to that shown in FIG. 1.

Device 20 illustrated in FIGS. 3 and 4 has particular utility when the matrices of reservoir layers 15 and 16 are composed, in whole or in part, of a hydrophilic material having a tendency to swell as it absorbs the hydrating liquid. This embodiment has particular advantage when using hydrophilic hydrogels as the matrices of reservoir layers 15 and 16, since hydrogels have a tendency to swell during hydration. Most preferably, the right side of device 20 is secured over the left side of device 20 after reservoir layers 15 and 16 have been completely hydrated and are no longer swelling.

When used in connection with the reservoir 15 or the donor electrode assembly 8, the term "agent" refers to beneficial agents, such as drugs, within the class which can be delivered through body surfaces. The expression "drug" is intended to have a broad interpretation as any therapeutically active substance which is delivered to a living organism to produce a desired, usually beneficial, effect. In general, this includes therapeutic agents in all of the major therapeutic areas including, but not limited to, anti-infectives such as antibiotics and antiviral agents, analgesics and analgesic combinations, anesthetics, anorexics, antiarthritics, antiasthmatic agents, anticonvulsants, antidepressants, antidiabetic agents, antidiarrheals, antihistamines, anti-inflammatory agents, antimigraine preparations, antimotion sickness preparations, antinauseants, antineoplastics, antiparkinsonism drugs, antipruritics, antipsychotics, antipyretics, antispasmodics, including gastrointestinal and urinary, anticholinergics, sympathomimetrics, xanthine derivatives, cardiovascular preparations including calcium channel blockers, beta-blockers, antiarrythmics, antihypertensives, diuretics, vasodilators, including general, coronary, peripheral and cerebral, central nervous system stimulants, cough and cold preparations, decongestants, diagnostics, hormones, hypnotics, immunosuppressives, muscle relaxants, parasympatholytics, parasympathomimetrics, proteins, peptides, psychostimulants, sedatives and tranquilizers.

The invention is particularly useful in the controlled delivery of peptides, polypeptides, proteins, macromolecules and other drugs which have a tendency to be unstable, hydrolyzed, oxidized, denatured or otherwise degraded in the presence of the liquid, such as water, necessary to conduct iontophoresis. For example, drugs containing either an ester bond (i.e., steroids) or an amide bond (i.e., peptides) may be hydrolyzed in water. Specific examples of drugs which can become degraded in the presence of water include catachols, such as apomorphine and epinephrine, salbutamol, sulfhydryls such as captopril, niphedipine, and peptides such as VIP and insulin.

Examples of other peptides and proteins which may be delivered using the device of the present invention include, without limitation, LHRH, LHRH analogs such as buserelin, gonadorelin, naphrelin and leuprolide, GHRH, insulin, heparin, calcitonin, endorphin, TRH, NT-36 (chemical name: N=[[(s)-4-oxo-2-azetidinyl]carbonyl]-L-histidyl-L-prolinamide), liprecin, pituitary hormones (e.g., HGH, HMG, HCG, desmopressin acetate, etc.), follicle luteoids, αANF, growth factor releasing factor (GFRF), βMSH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, hyaluronidase, interferon, interleukin-2, menotropins (urofollitropin (FSH) and LH), oxytocin, streptokinase, tissue plasminogen activator, urokinase, vasopressin, ACTH analogs, ANP, ANP clearance inhibitors, angiotensin II antagonists, antidiuretic hormone agonists, antidiuretic hormone antagonists, bradykinin antagonists, CD4, ceredase, CSF's, enkephalins, FAB fragments, IgE peptide suppressors, IGF-1, neurotrophic factors, parathyroid hormone and agonists, parathyroid hormone antagonists, prostaglandin antagonists, pentigetide, protein C, protein S, renin inhibitors, thymosin alpha-1, thrombolytics, TNF, vaccines, vasopressin antagonist analogs, alpha-1 anti-trypsin (recombinant).

When used in connection with the reservoir layer 16 and/or the counter electrode assembly 9, the term "agent" refers to any suitable pharmacologically acceptable electrolyte salt. Suitable electrolyte salts include water soluble and biocompatible salts such as sodium chloride, alkali metal salts, alkaline earth metal salts such as chlorides, sulfates, nitrates, carbonates, phosphates, and organic salts such as ascorbates, citrates, acetates and mixtures thereof.

Electrodes 11 and 12 are electrically conductive and may be formed of a metal, or other electrically conductive material. For example, electrodes 11 and 12 may be formed of a metal foil or metal deposited or painted on a suitable backing. Examples of suitable metals include silver, zinc, silver/silver chloride, aluminum, platinum, stainless steel, gold and titanium. Alternatively, the electrodes 11 and 12 may be formed of a polymer matrix containing a conductive filler such as a metal powder, powdered graphite, carbon fibers or other known electrically conductive filler material. The polymer based electrodes may be made by mixing the conductive filler in a preferably hydrophobic polymer matrix. For example, zinc powder, silver powder, silver/silver chloride powder, powdered carbon, carbon fibers and mixtures thereof can be mixed in a hydrophobic polymer (e.g., an ethylene vinyl acetate copolymer) matrix, with the preferred amount of conductive filler being within the range of about 30 to 90 vol % and the remainder being the hydrophobic polymer matrix.

Electrodes 11 and 12 are electrically connected to the power source in layer 14 using well known means, e.g., printed flexible circuits, metal foils, wires or by direct contact. As an alternative to a battery as the power source, device 10 can be powered by a galvanic couple formed by the donor electrode 11 and counter electrode 12 being composed of dissimilar electrochemical couples and being placed in electrical contact with one other. Typical galvanic couple materials for delivering a cationic agent include a zinc donor electrode 11 and a silver/silver chloride counter electrode 12. A Zn—Ag/AgCl galvanic couple provides an electrical potential of about 1 volt.

The optional wicking layers 23 and 24 may be comprised of liquid-wicking materials such as cotton, sponges, cellulose triacetate, rayon, polyesters, hydrophilic polymer resins, etc. and blends thereof. Optionally, the passageways 21 and 22 may be filled with the same or similar liquid-wicking material.

The matrix of reservoir layers 15 and 16 can be any material adapted to absorb and hold a sufficient quantity of liquid therein in order to permit transport of agent therethrough by iontophoresis. For example, gauzes made of cotton or other absorbent fabrics as well as pads and sponges, both natural and synthetic, may be used. Most preferably, the matrix of reservoir layers 15 and 16 is composed, at least in part, of a hydrophilic polymer material. Both natural and synthetic hydrophilic polymers may be used. Suitable hydrophilic polymers include copolyesters such as Hytrel sold by DuPont de Nemours & Co. of Wilmington, Del., polyvinylpyrrolidones, polyvinyl alcohol, polyethylene oxides such as Polyox ® manufactured by Union Carbide Corp., Carbopol ® manufactured by BF Goodrich of Akron, Ohio.; blends of polyoxyethylene or polyethylene glycols with polyacrylic acid such as Polyox ® blended with Carbopol ®, polyacrylamide, Klucel ®, cross-linked dextran such as Sephadex (Pharmacia Fine Chemicals, AB, Uppsala, Sweden), Water Lock ® (Grain Processing Corp., Muscatine, Iowa) which is a starch-graft-poly(sodium acrylate-co-acrylamide) polymer, cellulose derivatives such as hydroxyethyl cellulose, hydroxypropylmethylcellulose, low-substituted hydroxypropylcellulose, and cross-linked Na-carboxymethylcellulose such as Ac-Di-Sol (FMC Corp., Philadelphia, Pa.), hydrogels such as polyhydroxyethyl methacrylate (National Pat. Development Corp.), natural gums, chitosan, pectin, starch, guar gum, locust bean gum, and the like, along with blends thereof. Of these, polyvinylpyrrol idones are preferred.

Optionally, the matrix of reservoir layers 15 and 16 may also contain a hydrophobic, preferably heat fusible, polymer in order to enhance the lamination of reservoir layers 15 and 16 to the adjacent layers. Suitable hydrophobic polymers for use in the matrix of reservoir layers 15 and 16 include, without limitation, polyethylene, polypropylene, polyisoprenes and polyalkenes, rubbers, copolymers such as Kraton ®, polyvinylacetate, ethylene vinyl acetate copolymers, polyamides such as nylons, polyurethanes, polyvinylchloride, acrylic or methacrylic resins such as polymers of esters of acrylic or methacrylic acid with alcohol such as n-butanol, n-pentanol, isopentanol, 2-methyl butanol, 1-methyl butanol, 1-methyl pentanol, 2-methyl pentanol, 3-methyl pentanol, 2-ethyl butanol, isooctanol, n-decanol, or n-dodecanol, alone or copolymerized with ethylenically unsaturated monomers such as acrylic acid, methacrylic acid, acrylamide, methacrylamide, N-alkoxymethyl acrylamides, N-alkoxymethyl methacrylamides, N-tert-butylacrylamide, and itaconic acid, N-branched alkyl maleamic acids wherein the alkyl group has 10–24 carbon atoms, glycol diacrylates, and blends thereof. Most of the above listed hydrophobic polymers are heat fusible. Of these, ethylene vinyl acetate copolymers are preferred.

When the drug or electrolyte is present in the reservoir matrix before hydration, blending of the drug or electrolyte with the hydrophilic polymer matrix components can be accomplished mechanically, either by milling, extrusion or hot melt mixing, for example. The resulting reservoir layers may then be prepared by solvent casting, extrusion or by melt processing, for example. In addition to the drug and electrolyte, the reservoirs 15 and 16 may also contain other conventional materials such as dyes, pigments, inert fillers, and other excipients.

Insulator 26 is preferably formed of a hydrophobic non-conducting polymeric material which is impermeable to both the passage of ions and water. Preferred insulating materials are nonporous ethylene vinyl acetate and closed cell foamed plastics.

The combined skin-contacting areas of electrode assemblies 8 and 9 can vary from less than 1 cm$^2$ to greater than 200 cm$^2$. The average device 10 however, will have electrode assemblies with a combined skin-contacting area within the range of about 5 to 50 cm$^2$.

Having thus generally described our invention and described in detail certain preferred embodiments thereof, it will be readily apparent that various modifications to the invention may be made by workers skilled in the art without departing from the scope of this invention and which is limited only by the following claims.

What is claimed is:

1. A multilaminate dry state electrode assembly for an electrically powered iontophoretic agent delivery device including a source of electrical power which is electrically connected to the electrode assembly, the electrode assembly including:
   a) a reservoir layer including a substantially non-hydrated hydratable matrix containing an agent to be delivered through a body surface;
   b) an electrode layer in electrical contact with both the reservoir layer and the power source;
   c) means for hydrating the substantially non-hydrated agent containing matrix, said means including a preformed sealable passageway through the electrode layer, the passageway when unsealed establishing fluid communication between the exterior of the device and the matrix, said means enabling a liquid from an external source to be introduced through the passageway and into the reservoir matrix in order to hydrate the matrix and activate the electrode assembly; and
   d) means for sealing the passageway after introducing the liquid therein.

2. A multilaminate dry state electrode assembly for an electrically powered iontophoretic agent delivery device, the electrode assembly having a reservoir layer containing an agent to be delivered through a body surface and an electrode layer adapted to be place in electrical contact with both the reservoir layer and a power source, the reservoir layer comprising a substantially non-hydrated, hydratable matrix which is initially isolated from the power source, the reservoir layer having an exposable surface for introducing a liquid thereto to hydrate the reservoir layer, the reservoir layer being adapted to be placed in electrical contact with the power source after hydration of the reservoir layer, wherein both the power source and the reservoir layer are positioned on a sheet in spaced apart relation, the reservoir layer being releasably attached to the sheet.

3. The electrode assembly of claim 1 or 2, wherein the agent is unstable or becomes degraded in the presence of the liquid.

4. The electrode assembly of claim 1 or 2, wherein the electrode assembly is a donor electrode assembly and the agent is a drug.

5. The electrode assembly of claim 4, wherein the liquid comprises water.

6. The device of claim 1 or 2, wherein the electrode assembly is a counter electrode assembly and the agent is an electrolyte.

7. The device of claim 6, wherein the electrolyte is a water soluble electrolyte salt.

8. The device of claim 7, wherein the liquid comprises water.

9. The device of claim 7, wherein the liquid comprises an aqueous solution or an aqueous suspension of the electrolyte.

10. The device of claim 1 or 2, wherein the multilaminate electrode assembly includes an ion-conducting adhesive layer adapted to secure the electrode assembly to the body surface.

11. The device of claim 1 or 2, wherein the multilaminate electrode assembly includes a semipermeable membrane layer positioned between the reservoir layer and the body surface.

12. The device of claim 1 or 2, wherein the reservoir layer is comprised of a hydrophilic polymer.

13. The device of claim 1 or 2, wherein the matrix comprises a mixture of a hydrophilic polymer and a hydrophobic polymer.

14. The device of claim 1 or 2, wherein the power source comprises a battery.

15. The device of claim 1 or 2, wherein the body surface is intact skin or a mucosal membrane.

16. The device of claim 1, including a sealing cover layer formed on the outside of the electrode assembly, the passageway extending through both the electrode layer and the sealing cover layer.

17. The device of claim 1, wherein the preformed passageway contains a liquid wicking material.

18. The device of claim 1, including a layer of a liquid wicking material positioned adjacent the reservoir layer, the passageway extending from the exterior of the device, through the electrode layer to the liquid wicking material layer.

19. The device of claim 1, wherein the reservoir layer has a plurality of grooves in fluid communication with the passageway, said grooves being adapted to convey the liquid introduced through the passageway across the reservoir layer.

20. The electrode assembly of claim 1, wherein the means for sealing the passageway forms a water-tight seal.

21. The electrode assembly of claim 20, wherein the means for sealing the passageway comprises a plug.

22. The device of claim 2, wherein the reservoir layer is comprised of a liquid-swellable material.

23. The device of claim 2, wherein the sheet is adapted to be severed intermediate the power source and the reservoir layer.

24. The device of claim 2, wherein the reservoir layer is intermediate the sheet and a release liner.

25. The device of claim 2, wherein the sheet comprises a water impermeable backing material.

26. The device of claim 2, wherein the sheet has a weakened score line between the agent reservoir layer and the electrode layer.

27. An electrically powered iontophoretic agent delivery device comprising:
  a) a source of electrical power;
  b) a multilaminate dry state donor electrode assembly having a reservoir containing a drug to be delivered through a body surface and a donor electrode in electrical contact with both the drug reservoir and the power source;
  c) a multilaminate dry state counter electrode assembly having a reservoir containing an electrolyte and an electrode in electrical contact with the electrolyte reservoir and the power source;
  wherein each of the drug reservoir and the electrolyte reservoir comprises a substantially non-hydrated, hydratable matrix which is positioned on a sheet in spaced apart relation to the power source, each of the drug reservoir and electrolyte reservoir having an exposable surface for introducing a hydrating liquid water thereto to hydrate same, the drug reservoir being adapted to be placed in electrical contact with the donor electrode and the electrolyte reservoir being adapted to be placed in electrical contact with the counter electrode after hydration of said reservoirs.

28. The device of claim 20, further comprising an ion-impermeable separator positioned between the electrode assemblies, wherein the separator is comprised of hydrophobic polymer.

29. A method of hydrating a dry state multilaminate electrode assembly in an electrically powered iontophoretic agent delivery device, the electrode assembly including a substantially non-hydrated hydratable reservoir layer containing an agent to be delivered and an electrode layer in electrical contact with both a power source and the reservoir layer, the method comprising:
  introducing a liquid from an external source through a preformed sealable passageway, the passageway when unsealed extending from the exterior of the device through the electrode layer and into the hydratable reservoir layer; and
  sealing the passageway after introducing the liquid therein.

30. A method of hydrating a dry state multilaminate electrode assembly in an electrically powered iontophoretic agent delivery device, the electrode assembly including a non-hydrated hydratable reservoir layer containing an agent to be delivered and an electrode layer adapted to be placed in electrical contact with both the reservoir layer and an electrical power source, the method comprising:
  a) positioning the agent containing reservoir layer and the power source on a sheet in spaced apart relation while the agent containing reservoir layer is in a substantially non-hydrated condition, the reservoir layer being releasably attached to the sheet;
  b) introducing a hydrating liquid into the reservoir layer in an amount sufficient to permit ion transport through the reservoir layer; and thereafter
  c) electrically connecting the hydrated reservoir layer to the power source.

31. The method of claim 29 or 30, wherein the agent is unstable or becomes degraded in the presence of the liquid.

32. The method of claim 29 or 30, wherein the electrode assembly is a donor electrode assembly and the agent is a drug.

33. The method of claim 29 or 30, wherein the liquid comprises water.

34. The method of claim 29 or 30, wherein the electrode assembly is a counter electrode assembly and the agent is an electrolyte.

35. The method of claim 34, wherein the electrolyte comprises a water soluble electrolyte salt.

36. The method of claim 29 or 30, wherein the liquid comprises water.

37. The method of claim 29 or 30, wherein the liquid is an aqueous solution or an aqueous suspension of an electrolyte.

38. The method of claim 29 or 30, wherein the reservoir layer is comprised of a non-hydrated hydrogel.

39. The method of claim 29 or 30, wherein the body surface is intact skin or a mucosal membrane.

40. The method of claim 29, including positioning a wicking layer in fluid communication with both the preformed passageway and the agent reservoir, the wicking layer being effective to distribute the liquid introduced through the passageway across a surface of the reservoir layer.

41. The method of claim 29, including providing a plurality of grooves in a surface of the reservoir layer, the grooves being in fluid communication with the preformed passageway, the grooves being effective to distribute the liquid introduced through the passageway across the reservoir layer.

42. The method of claim 29, wherein the sealing forms a water-tight seal.

43. The method of claim 29, including placing a plug in the passageway.

44. The method of claim 30, including positioning a wicking layer in fluid communication with the agent reservoir layer 45. The method of claim 30, including providing grooves in an accessible surface of the reservoir layer.

* * * * *